United States Patent [19]

Golovistikov et al.

[11] Patent Number: 6,040,187
[45] Date of Patent: Mar. 21, 2000

[54] METHOD OF DETERMINING THE SUPPRESSOR CELL COMPONENT OF HUMAN IMMUNE STATUS AND A MEANS FOR THE REALIZATION THEREOF

[75] Inventors: Ivan Nikolaevich Golovistikov, Russian Federation, Moscow, Donbasskaya str., 5, ap.51; Leonid Yazonovich Kacharava, Georgia, Tbilici, Mirtskhulava str., 2 ap.45; Khallar Abdumuslimovich Alikhanov, Moscow, all of Russian Federation

[73] Assignees: Ivan Nikolaevich Golovistikov, Moscow; Leonid Yazonovich Kacharava, Tbilici, both of Russian Federation

[21] Appl. No.: 08/716,138

[22] PCT Filed: Mar. 16, 1995

[86] PCT No.: PCT/RU95/00046

§ 371 Date: Jan. 21, 1997

§ 102(e) Date: Jan. 21, 1997

[87] PCT Pub. No.: WO95/25956

PCT Pub. Date: Sep. 28, 1995

[30] Foreign Application Priority Data

Mar. 18, 1994 [RU] Russian Federation ............. 94008170

[51] Int. Cl.[7] .................................................... G01N 33/48
[52] U.S. Cl. ............................ 436/63; 530/395; 530/397
[58] Field of Search ................................ 514/8; 530/395, 530/397; 435/7.2; 436/506, 63

[56] References Cited

U.S. PATENT DOCUMENTS

| 4,275,000 | 6/1981 | Ross ..................................... 260/112 R |
| 5,013,719 | 5/1991 | Bowlin ........................................ 514/11 |
| 5,118,669 | 6/1992 | Noguchi et al. ........................... 514/17 |
| 5,141,849 | 8/1992 | Chou ............................................. 435/6 |
| 5,169,835 | 12/1992 | Chan ........................................ 514/8 |

FOREIGN PATENT DOCUMENTS

| 2650183 | 2/1991 | France . |
| 1061818 | 12/1983 | Russian Federation . |
| 1657190 | 6/1991 | Russian Federation . |
| 676467 | 4/1987 | Switzerland . |
| 1061818 | 12/1983 | U.S.S.R. . |
| 1657190 | 6/1991 | U.S.S.R. . |
| 2170707 | 8/1986 | United Kingdom . |
| 2251186 | 7/1992 | United Kingdom . |
| 8801875 | 3/1988 | WIPO . |
| 8805297 | 7/1988 | WIPO . |
| 9110443 | 7/1991 | WIPO . |

OTHER PUBLICATIONS

Effect on Pregnancy and Hormonal Changes on the Activity of Rheumatoid Arthritis Monika Ostensen, et al, Dept. of Rheumatology, Institute of Clinical Medicine, Univ. of Tromso, Norway, Scand J. Rheum. 12:69 –72, 1983.

Suppressor Cell Activity After Concanavalin A Treatment of Lymphocytes from Normal Donors, Shou, et al, Journal of Experimental Medicine vol. 143, 1100–111;1976.

Inhibitory and Stimulatory Effects of Concanavalin on the Response of Mouse Spleen Cell Suspensions to Antigen, Richard Dutton, Journal of Experimental. Medicine vol. 138, pp. 1496–1505 (1973).

Immunochemical Identification of New Beta–1–Globulin in the Blood Serum of Pregnant Women, Bulletin of Experimental Biology and Medicine, 1970 No. 6, Medicina Publishers, Moscow, pp. 66–68, Figs. 1–2.

Human Trophoblastic Beta–1–Globulin and Chorionepithelioma, Tatarinov, et al, Onco Developmental Gene Expression, 1976, pp. 463–468.

Reference Preparation for Assay of Some Pregnancy and Cancer Associates Proteins, The Lancet, Oct. 11, 1980.

Shou, L., et al., "Suppressor Cell Activity After Concanavalin A Treatment of Lymphocytes From Normal Donors" *The Journal of Experimental Medicine*, vol. 143, 1976, pp. 1100–1109.

Dutton, R., "Inhibitory and Stimulatory Effects of Concanavalin A on the Response of Mouse Spleen Cell Suspensions to Antigen" *The Journal of Experimental Medicine*, vol. 138, 1973, pp. 1496 to 1505.

Shou et al., J.Exp.Med. 143(5):1100–1116, May 1976.

Gorlina et al, The Soviet Journal of Developmental Biology (English translation of Ontogenez) 14 (6):366–369, Sep. 1984.

Golovistikov et al., Immunologiya, 1:76–78, 1987.

*Primary Examiner*—Lorraine Spector
*Assistant Examiner*—Eliane Lazar-Wesley

[57] ABSTRACT

The method for determining a suppressor component of human immune status comprises collecting peripheral blood, obtaining a suspension of mononuclear cells (MNCs), dividing said suspension into two equal portions, cultivating MNCs in the first portion without a suppressor activator, cultivating MNCs in the second portion with said suppressor activator (TBG), washing MNCs out of culture medium, blocking the proliferation, adding newly isolated MNCs from a normal donor, which MNCs have been stimulated with phytohemagglutinin, into each of MNC portions in equal proportions to obtain test cultures, cultivating said test cultures, further evaluating the proliferation in said test cultures and determining the suppression value on the basis of the ratios of proliferation levels in test cultures.

13 Claims, No Drawings

METHOD OF DETERMINING THE SUPPRESSOR CELL COMPONENT OF HUMAN IMMUNE STATUS AND A MEANS FOR THE REALIZATION THEREOF

This application is a national stage entry of PCT/Ru95/00046 filed Mar. 16, 1995.

FIELD OF TECHNOLOGY

The present invention relates to medicine, more specifically to the method of diagnostic evaluation of T-suppressors activity, namely, to the method for determining a suppressor component of human immune status and to the means for the realization thereof.

PRIOR ART

Known is β-I-glycoprotein of placental origin which is a of trophoblastic β-I-glycoprotein (TBG) used as a growth and proliferation stimulator for hematopoietic blood cells (U.S. Pat. No. 5,169,835, cl. A61K 35/50, 1989).

Nevertheless the known compound has not been used for determining a suppressor component of human immune status.

Known is the use of TBG for diagnosing and prognosticating the course of pregnancy (see L. G. Sotnikova et al., *The Role of β-I-glycopzotein Trophoblast in Diagnosing and Prognosticating Pregnancy*, Metodicheskije Recomendatsii, Moscow, 1984). Nevertheless said work does not disclose the possibility of using TBG for diagnosing a suppressor component of human immune status.

Known is method for determining a suppressor component of human immune status which comprises collecting peripheral blood, obtaining a suspension of pure lymphocytes for cultivating test cultures with a suppression activator and without such activator, and further evaluating proliferation levels (see Dutton R. W. *Inhibitory and Stimulatory Effects of Concanavalin A on the Response of Mouse Spleen Cells Suspensions to Antigen*. J. Exp. Med., v.138, p.1496–1505, 1973).

Nevertheless the known method requires a hardly available and expensive foreign preparation, that is concanavalin A, as a suppression activator.

Known is a method for determining a suppressor component of human immune status which comprises collecting peripheral blood, obtaining a suspension of mononuclear cells (MNCs), dividing said suspension into two equal portions, cultivating MNCs from the first portion without a suppressor activator, and cultivating MNCs from the second portion with a suppressor activator, washing MNCs out of the culture medium and blocking proliferation, adding newly isolated MNCs from a normal donor into each of abovementioned portions of MNCs, stimulating with phytohemagglutinin in equal proportions to obtain test cultures, cultivating them and further evaluating proliferation in said test cultures and determining suppression value on the basis of the raties of proliferation levels in said test cultures (see By Lien Shov, Stanley A. Schwarts and Robert A. Good. *Suppressor Cell Activity after Concanavalin A treatment of Lymphocytes from Normal Donors*. J. Exp. Med., 1976, v.143, n.5, p. 1100–1110).

Nevertheless said known method also requires a hardly available and expensive foreign preparation, concanavalin A.

SUMMARY OF THE INVENTION

The main object of the present invention is to provide a less expensive process for determining a suppressor activity of human immune status by using a well available preparation which has an immune correcting activity and does not cause allergic reactions.

Said object is achieved by use of trophoblastic β-I-glycoprotein (TBG) as a means for determining a suppressor component of human immune status, and the method of determination of a suppressor component of human immune status which method comprises collecting a sample of peripheral blood, obtaining a suspension of mononuclear cells (MNCs), dividing said suspension into two portions, cultivating the first portion without a suppressor activator, and cultivating the second one with a suppressor activator, washing MNCs out of the culture medium, blocking proliferation, adding into each of said MNC portions newly isolated MNCs obtained from a normal donor, stimulating with phytohemagglutinin in equal proportions to produce test cultures, cultivating said cultures, further evaluating the proliferation of said cultures and determining the suppression values based on the ratios of the levels of proliferation in test cultures. According to the present invention trophoblastic β-I-glycoprotein (TBG) is used in dosages from 3 to 120 µg per 1 ml of MNC suspension.

The MNC suspension may be prepared from the cells obtained as a result of separation in phycoll-urotrust single-step gradient, MNCs cultivation being carried out during 48 hours. Proliferation may be blocked by treating MNCs with mitomycin C, and each of the test cultures may be cultivated during 72 hours.

Experiments and clinical tests have shown new properties of TBG as suppressor activator useful for the determination of suppressor component of human immune status.

PREFERRED EMBODIMENT OF THE INVENTION

At the first step MNC suspension is prepared from the cells obtained as a result of the separation in phycoll-urotrust single-stage density gradient (Boyum's method).

Peripheral blood is taken from a patient by venipuncture and placed simultaneously into the tubes containing heparine solution (1 ml of blood=20–30 heparine units). Then the blood is diluted with Hanks solution in proportion 1:2 without $Ca^{++}$ and $Mg^{++}$ and layered onto phycoll-urotrust gradient (the density being 1.078).

Then centrifugation is carried out at 400 g during 30 min. MNC dispersion from interphase is placed into a centrifuge tube, Hanks solution without $Ca^{++}$ and $Mg^{++}$ is added, and 3 successive centrifugations are carried out (10 in each) to wash the cells out of phycoll-urotrust solution. After the third centrifugation MNC residue is resuspended in 1 ml of 199 medium, and the number of mononuclear cells is counted using Goryajev camera.

At the second stage MNCs are divided into 2 equal portions, the first portion is cultivated without a suppressor activator, and a second one is cultivated with the suppressor activator, and trophoblastic β-I-glycoprotein (TBG) is used as said activator.

MNCs are cultivated in penicillin vessels with 14.5 rubber plugs at 37° C. The culture medium is PPMI-1640 with 20% serum of IV (AB) group and 300 mg of glutamine.

Each vessel contains $5\times10^6$ cells in 2.0 ml of complete medium.

TBG in the dosages of 3–120 µg is added into the culture to induce suppressor.

Cells are cultivated during 48 hours. Then MNCs are washed out of the culture medium and the proliferation is blocked by treating with mitomycin C (40 μg/ml during 30 min. at 37°). Then washing is performed three times using 199 medium with 5% IV (AB) serum (chilled). Cell residue is resuspended, the number of nucleus—containing cells is counted, the percentage of cells viability is determined using 0.1% trypane blue solution, and the resulting suspension is diluted to the required concentration. All operations are carried out separately for the control cells, and for the TBG stimulated cells, and the silicone dishes are used to wash the cells.

At the next step newly isolated lymphocytes from a normal donor (which lymphocytes are prestimulated with phytohemagglutinin (PHA) and used as responding test cells) are added into each of the portions of control and TBG—stimulated lymphocytes in equal proportion ($0.5 \times 10^6 : 0.5 \times 10^6$ cells/ml) in order to obtain test cultures. The cultivation is carried out during 72 hours. Then the proliferation of test cultures is evaluated using $H^3$-thymidine, and the suppression is evaluated by the degree of proliferation decrease therein. Suppression index is determined using the following formula:

$$SI=(1-\text{pulse number/min. in test culture with TBG/pulse number/min. in test cultures without TBG}) \times 100\%$$

To evaluate the suppressor component in a normal donor a diagnostic study according to a known method (see By Lien Shov, Stanley A. Schwarts and Robert A. Good. *Suppressor Cell Activity after Concanavalin A Treatment of Lymphocytes from Normal Donors*. J.Exp.Med., 1976, v.143, n.5, p. 1100–1110), as well as a diagnostic study according to the method of the present invention have been carried out using a group of normal donors (100 persons). Based on the results thus obtained the normal value of T-suppressors activity under the induction with concanavalin A is determined as 56.8% ±4%, while according to the method of the present invention such value is 63.4% ±4.7%.

Further disclosure of the invention is provided in the following examples.

EXAMPLE 1

Patient V., 30, came to the hospital with the diagnosis of "disseminated sclerosis, celebromedullary form" in acute stage. T-suppressors activity in peripheral blood under concanavalin A induction was 15%, which value had been determined according to the known method for evaluation of the suppressor component of human immune status. Simultaneously T-suppressors activity in peripheral blood from the same patient was determined using the method according to the present invention (under TBG induction), and the value thus obtained was 17%.

EXAMPLE 2

Patient S. (female), 40, came to the hospital with the diagnosis of "disseminated sclerosis, celebromedullary form" in acute stage. T-suppressors activity in peripheral blood under concanavalin A induction (determined according to the known method) was 16%. Simultaneously T-suppressors activity in peripheral blood in the same patient was determined using the method according to the present invention (under TBG induction), and the value thus obtained was 19%.

150 patients suffering disseminated sclerosis and rheumatoid arthritis have been studied. It has been shown that T-suppressors activity determined by the method according to the invention corresponds to the values obtained by the known method.

Therefore high efficiency of TBG as a means for determining the suppressor component of human immune status has been confirmed.

INDUSTRIAL APPLICABILITY

Abovementioned advantages of the method for determining a suppressor component of human immune status according to the present invention, as well as those of the means used therein, enable wide usage of said method both for scientific purposes in clinical practice.

Also it should be noted that the use of concanavalin A for treating abovementioned diseases is counterindicative due to toxicity thereof, while TBG (produced by human trophoblast) shows no toxicity and does not cause allergic reactions. This fact enables to use said preparation as a drug.

What is claimed is:

1. A method for determining a suppressor component of a patient's immune status comprising:

(a) preparing first and second suspensions comprising mononuclear cells of the patient;

(b) cultivating the mononuclear cells of the first suspension with a suppressor activator consisting essentially of trophoblastic β-1 glycoprotein (TBG) in an amount effective to induce activation of suppressors in the mononuclear cells of the first suspension;

(c) cultivating the mononuclear cells of the second suspension without a suppressor activator;

(d) blocking proliferation of the mononuclear cells in each of the first and second suspensions;

(e) adding responder cells to each of the first and second suspensions in equal amounts so as to obtain respective first and second test cultures;

(f) cultivating the first and second test cultures under conditions that cause the responder cells to proliferate; and (g) determining the suppressor component of the immune system of the patient by comparing respective proliferation of the responder cells in the first and second test cultures and assessing the suppressor component based on the extent, if any, that proliferation of the responder cells of the first test culture is lower than proliferation of the responder cells of the second test culture.

2. The method as claimed in claim 1, wherein the responder cells are mononuclear cells from a normal donor that have been treated to cause them to proliferate.

3. The method as claimed in claim 2, wherein the responder cells have been treated with phytohemagglutinin.

4. The method as claimed in claim 2, wherein the first and second suspensions are prepared in step (a) by obtaining a sample of peripheral blood from the patient and separating the mononuclear cells in a phycoll-urotrust single-step gradient.

5. The method as claimed in claim 2, wherein step (d) comprises treating the mononuclear cells with mitomycin C.

6. The method as claimed in claim 2, wherein in step (b) the mononuclear cells of the first suspension are cultivated with 3 to 120 μg of TBG per 1 ml of the first suspension.

7. The method as claimed in claim 6, wherein the cultivating in step (b) is carried out for about 48 hours.

8. The method as claimed in claim 2, wherein the cultivating in step (f) is carried out for about 72 hours.

9. In a method for determining a suppressor component of the immune status of a patient by comparing a proliferation of responder mononuclear cells in a first test culture with a proliferation of responder mononuclear cells in a second test culture, said first and second test cultures comprising respective first and second suspensions each of which comprises said responder cells and mononuclear cells of the patient, the mononuclear cells of the first suspension having been cultivated with a suppressor activator in the mononuclear cells of the patient, the mononuclear cells of the second suspension having been cultivated without a suppressor activator, the improvement wherein said suppressor activator is trophoblastic β-1 glycoprotein (TBG).

10. The method as claimed in claim 9, wherein the TBG is present in the first suspension in an amount of 3 to 120 μg per 1 ml of the mononuclear cells of the patient.

11. The method as claimed in claim 10, wherein the responder cells are mononuclear cells from a normal donor that have been treated to cause them to proliferate.

12. The method as claimed in claim 10, wherein the responder cells have been treated with phytohemagglutinin.

13. The method as claimed in claim 11, wherein the first and second suspensions are prepared by obtaining a sample of peripheral blood from the patient and separating the mononuclear cells in a phycoll-urotrust single-step gradient.

* * * * *